(12) United States Patent
Seko et al.

(10) Patent No.: US 11,624,698 B2
(45) Date of Patent: Apr. 11, 2023

(54) GAS SENSING APPARATUS

(71) Applicant: Tianma Japan, Ltd., Kanagawa (JP)

(72) Inventors: Nobuya Seko, Kanagawa (JP); Haruki Yamane, Akita (JP)

(73) Assignee: TIANMA JAPAN, LTD., Kanagawa (JP)

( * ) Notice: Subject to any disclaimer, the term of this patent is extended or adjusted under 35 U.S.C. 154(b) by 0 days.

(21) Appl. No.: 17/930,084

(22) Filed: Sep. 7, 2022

(65) Prior Publication Data
US 2023/0003638 A1  Jan. 5, 2023

Related U.S. Application Data

(63) Continuation of application No. 16/834,058, filed on Mar. 30, 2020, now Pat. No. 11,474,025.

(30) Foreign Application Priority Data

Mar. 29, 2019 (JP) .................................. 2019-067141

(51) Int. Cl.
*G01N 21/21* (2006.01)
*G01N 33/00* (2006.01)
*G01N 21/17* (2006.01)

(52) U.S. Cl.
CPC ........... *G01N 21/21* (2013.01); *G01N 33/005* (2013.01); *G01N 2021/1727* (2013.01); *G01N 2201/067* (2013.01)

(58) Field of Classification Search
None
See application file for complete search history.

(56) References Cited

U.S. PATENT DOCUMENTS

| | | |
|---|---|---|
| 3,440,430 A | 4/1969 | Tansley |
| 4,890,290 A | 12/1989 | Hawkins, II |
| 4,974,219 A | 11/1990 | Korth |
| 5,108,185 A | 4/1992 | Mansuripur et al. |
| 5,245,408 A | 9/1993 | Cohen |
| 5,309,912 A | 5/1994 | Knüttel |

(Continued)

FOREIGN PATENT DOCUMENTS

| | | |
|---|---|---|
| JP | 7-159321 A | 6/1995 |
| JP | 8-15130 A | 1/1996 |

(Continued)

OTHER PUBLICATIONS

Office Action issued in Japanese Patent Application No. 2019-067141 dated Dec. 13, 2022. (English Translation w/ Concise Explanation of the Relevance Provided).

*Primary Examiner* — Rufus L Phillips
(74) *Attorney, Agent, or Firm* — Nixon & Vanderhye

(57) ABSTRACT

A gas sensing element that reflects light incoming along an optical path on a sensing face, where the light reflected by the gas sensing element changes depending on a quantity of a specific gas that is in contact with the gas sensing element, and where each of a first optical fiber and a second optical fiber bends the optical path. The gas sensing element, a light source, a photodetector, and a magnetic field applicator are disposed on a same side with respect to a virtual plane that is perpendicular to an incident plane of the incoming light to the sensing face of the gas sensing element and includes a point on the optical path where light goes out from the first optical fiber and a point on the optical path where light enters the second optical fiber.

8 Claims, 12 Drawing Sheets

(56) References Cited

U.S. PATENT DOCUMENTS

| | | |
|---|---|---|
| 5,381,234 A | 1/1995 | Barbee et al. |
| 6,109,094 A | 8/2000 | Baranzahi et al. |
| 6,201,601 B1 | 3/2001 | Vaez-Iravani et al. |
| 6,982,789 B1 | 1/2006 | Meyer |
| 7,233,396 B1 | 6/2007 | Hall et al. |
| 9,097,677 B1 | 8/2015 | Miller |
| 9,170,156 B2 | 10/2015 | Li et al. |
| 10,292,589 B2 | 5/2019 | Wang et al. |
| 2002/0048019 A1 | 4/2002 | Sui et al. |
| 2005/0006590 A1 | 1/2005 | Harrison |
| 2006/0208198 A1 | 9/2006 | Harrison |
| 2010/0267165 A1 | 10/2010 | Bruls et al. |

FOREIGN PATENT DOCUMENTS

| | | |
|---|---|---|
| JP | 2002-131449 A | 5/2002 |
| JP | 2007-506976 A | 3/2007 |
| JP | 2012-122835 A | 6/2012 |
| JP | 2017-172993 A | 9/2017 |

GAS SENSING APPARATUS

CROSS-REFERENCE TO RELATED APPLICATIONS

This application is a Continuation of application Ser. No. 16/834,058, filed on Mar. 30, 2020, which claims priority under 35 U.S.C. § 119(a) to Application No. 2019-067141, filed in Japan on Mar. 29, 2019, all of which are hereby expressly incorporated by reference into the present application.

BACKGROUND

This disclosure relates to a gas sensing apparatus.

There is a known technology of hydrogen gas sensing utilizing magneto-optical effects of a laminate film (sensor element) including a gas sensing layer, a magnetic layer, an optical interference layer, and a reflective layer (for example, JP 2017-172993 A). The hydrogen gas sensor disclosed in JP 2017-172993 A detects hydrogen by illuminating the surface of the sensor element, detecting the reflection, and measuring the change in polarization angle. The major components of this hydrogen sensor of a light source, a photodetector, a sensing element, and a magnetic field applicator are disposed to sandwich the atmosphere to be examined. Specifically, the magnetic field generation mechanism is disposed behind the sensor element (on the substrate side of the sensor element) and the light source and the photodetector are disposed in front of the sensor element (on the film surface side of the sensor element).

SUMMARY

An aspect of this disclosure is a gas sensing apparatus including a light source, a photodetector, a gas sensing element disposed on an optical path from the light source to the photodetector, a first optical element disposed between the light source and the gas sensing element on the optical path, a second optical element disposed between the gas sensing element and the photodetector on the optical path, and a magnetic field applicator configured to apply a magnetic field to the gas sensing element. The gas sensing element reflects light incoming along the optical path on a sensing face. The light reflected by the gas sensing element changes in a characteristic depending on quantity of a specific gas that is in contact with the gas sensing element. Each of the first optical element and the second optical element bends the optical path. The gas sensing element, the light source, the photodetector, and the magnetic field applicator are disposed on the same side with respect to a virtual plane that is perpendicular to an incident plane of the incoming light to the sensing face of the gas sensing element and includes a point on the optical path where light goes out from the first optical element and a point on the optical path where light enters the second optical element.

It is to be understood that both the foregoing general description and the following detailed description are exemplary and explanatory and are not restrictive of this disclosure.

EMBODIMENTS

Hereinafter, embodiments of this disclosure are described with reference to the accompanying drawings. It should be noted that the embodiments are merely examples to implement this disclosure and not to limit the technical scope of this disclosure.

The aforementioned conventional hydrogen gas sensor applies light and a magnetic field to the sensing element to detect change of the gas sensing layer in the sensing element with light. The change of the gas sensing layer is caused by exposure of the surface of the sensing element to the atmosphere to be examined. The above-described structure has the light source and the photodetector on the atmosphere side and therefore, a mechanism to hold these components is required. The laminate film of the sensing element is extremely thin, which is approximately 200 nm (0.200 μm) even if the thicknesses of all layers are summed up. The thickness of the glass substrate to hold the laminate film thereon is approximately 0.5 mm (500 μm) and therefore, the sensing element is thin and small. However, the sensing element is located deep when seen from the atmosphere side because the light source, the photodetector, and the structure to hold these components are provided in front of the sensing element.

Accordingly, in an exemplary case where this gas sensor is used to detect hydrogen gas leakage, the atmosphere has to be guided to behind the components disposed over the gas sensing element in order to expose the surface of the gas sensing element to the atmosphere. The structure becomes complicated and the restriction for installation increases.

The described hereinafter are embodiments of a gas sensing apparatus. One of the features of the gas sensing apparatus described herein is disposition of components. The specific disposition of the components provides open space in front of the sensing face (surface) of the gas sensing element, which reduces the restriction for installing the gas sensing apparatus.

Embodiment 1

Figure 1:
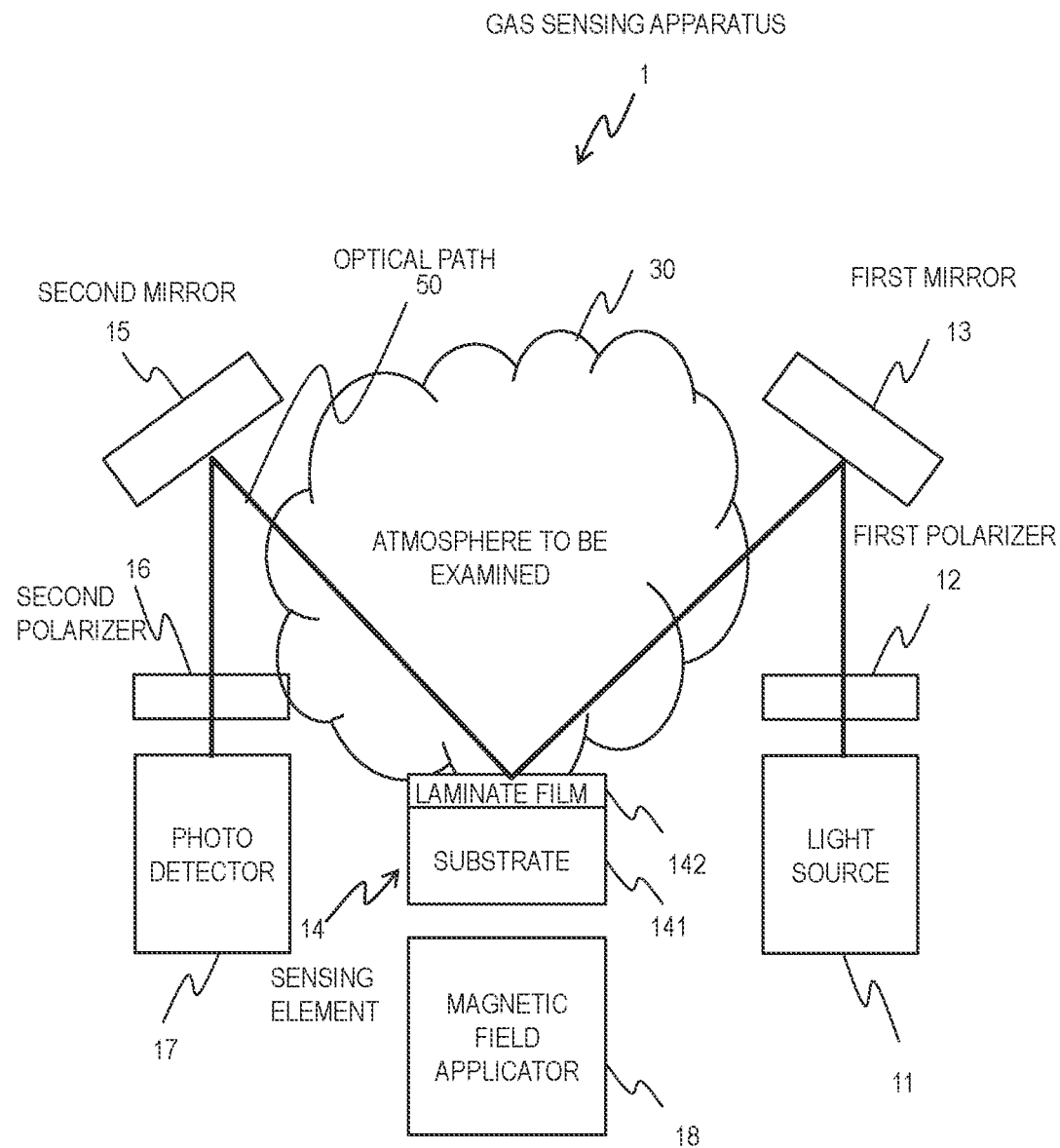
FIG. 1 schematically illustrates a configuration example of a gas sensing apparatus in Embodiment 1.

FIG. 1 schematically illustrates a configuration example of a gas sensing apparatus 1 in an embodiment. The gas sensing apparatus 1 includes a light source 11, a first polarizer 12, a first mirror 13, a gas sensing element (also referred to simply as sensing element) 14, a second mirror 15, a second polarizer 16, a photodetector 17, and a magnetic field applicator 18. The gas sensing element 14 includes a substrate 141 and a laminate film 142 provided on the substrate 141. The surface of the laminate film 142 is exposed to atmosphere 30 to be examined which may include the gas to be detected.

The gas sensing apparatus 1 detects the target gas by measuring the change in magneto-optic effect (magnetic Kerr effect) of the gas sensing element 14 caused by the target gas. More specifically, the gas sensing apparatus 1 detects the target gas by measuring change of light as the change in the magneto-optic effect of the laminate film 142 caused by the target gas.

The light source 11 generates and emits light (measuring light) to illuminate the laminate film 142. The light from the light source 11 is reflected by the laminate film 142 and the photodetector 17 detects the light reflected by the laminate film 142. On the optical path 50 from the light source 11 to the photodetector 17, the first polarizer 12 and the first mirror 13 are disposed between the light source 11 and the gas sensing element 14.

In the configuration example illustrated in FIG. 1, the first polarizer 12 is disposed between the light source 11 and the first mirror 13 on the optical path 50. Further on the optical path 50, the second mirror 15 and the second polarizer 16 are disposed between the gas sensing element 14 and the photodetector 17. In the configuration example illustrated in FIG. 1, the second polarizer 16 is disposed between the second mirror 15 and the photodetector 17 on the optical path 50.

The magnetic field applicator 18 is disposed on the opposite side of the mirrors 13 and 15 with respect to the gas sensing element 14. In the example in FIG. 1, the magnetic field applicator 18 is disposed under the gas sensing element 14 and the mirrors 13 and 15 are disposed above the laminate film 142. In the example in FIG. 1, the gas sensing element 14 is disposed between the light source 11 and the photodetector 17 when seen in the direction normal to the sensing face of the laminate film 142.

When seen in the direction normal to the sensing face of the laminate film 142, the magnetic field applicator 18 overlaps the gas sensing element 14 at least in a part. In FIG. 1, the underside of the magnetic field applicator 18 is located far from the sensing face of the laminate film 142, compared to the underside of the gas sensing element 14. The magnetic field applicator 18 is disposed between the light source 11 and the photodetector 17 when seen in the direction normal to the sensing face of the laminate film 142.

The light source 11 generates and emits light to illuminate the gas sensing element 14. The light source 11 can be a semiconductor laser or a light-emitting diode. The light from the light source 11 includes a specific wavelength suitable for gas detection with the laminate film 142; an example of the light is monochromatic light having the specific wavelength. The first polarizer 12 transmits light oscillating in a specific direction (linearly polarized light) out of the incoming light and attenuates light oscillating in the other directions. In other words, the first polarizer 12 generates linearly polarized light from the light of the light source 11.

Although this configuration example generates linearly polarized light with the light source 11 and the first polarizer 12, another configuration example can employ a light source that outputs linearly polarized light like a semiconductor laser including a polarizer therein to omit the first polarizer 12. Unlike the configuration example in FIG. 1, the first polarizer 12 can be disposed between the first mirror 13 and the gas sensing element 14 on the optical path 50.

The first mirror 13 reflects light transmitted through the first polarizer 12 to bend the optical path 50. The linearly polarized light reflected by the first mirror 13 hits the laminate film 142 of the gas sensing element 14. The magnetic field applicator 18 applies a magnetic field to the laminate film 142. The direction of the magnetic field is parallel to or perpendicular to the surface of the laminate film 142.

When the laminate film 142 with a magnetic field being applied reflects incoming light, the characteristics (such as polarization angle and intensity) of the reflected light are changed by the magneto-optic effect of the laminate film 142 to be different from the characteristics of the incoming light. Meanwhile, the characteristics of the reflected light vary depending on whether the target gas exists or not and further, the density of the target gas. The reflected light hits the second mirror 15.

The light reflected by the second mirror 15 enters the second polarizer 16. The second polarizer 16 transmits light oscillating in a specific direction (linearly polarized light) out of the incoming light and attenuates light oscillating in the other directions. The second polarizer 16 enables the characteristics change caused by the magneto-optic effect of the laminate film 142 to be detected from the reflected light. Specifically, under the configuration such that the characteristics change in the reflected light is observed as change in polarization angle like polar Kerr effect or longitudinal Kerr effect, the second polarizer 16 transforms the characteristics change in the reflected light into a change in light intensity. The light transmitted through the second polarizer 16 enters the photodetector 17. The photodetector 17 measures the intensity of the incoming light. More optical elements can be added to the configuration in FIG. 1; for example, a wavelength filter to transmit light having a specific wavelength as the light emitted from the light source 11 can be provided between the second mirror 15 and the photodetector 17.

Figure 2:
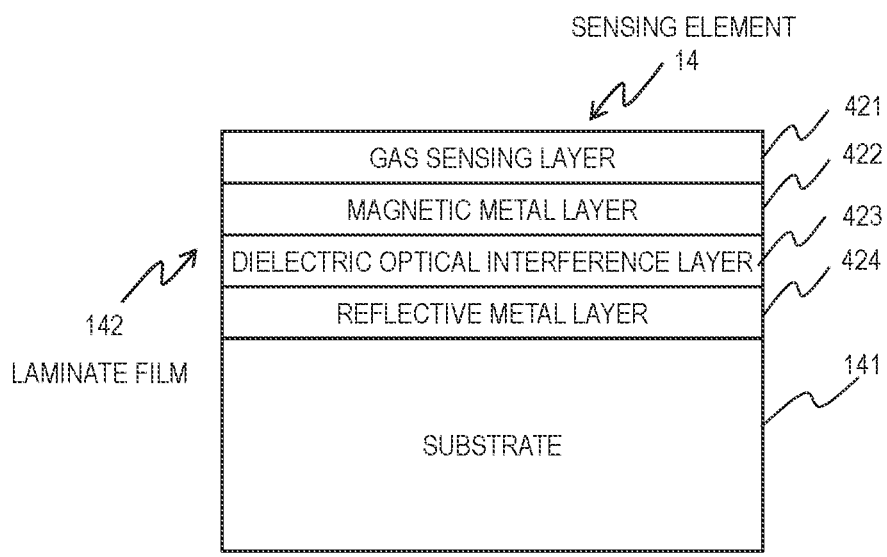
FIG. 2 illustrates an example of a laminate structure of a gas sensing element in Embodiment 1.

FIG. 2 illustrates an example of the laminate structure of the gas sensing element 14. FIG. 2 is an example of a hydrogen gas sensing element. A laminate film 142 is provided on a substrate 141. The laminate structure (such as the material of each layer, the number of layers, the order of layers, and the thickness of each layer) of the laminate film 142 is selected appropriately to adjust the detectable density range for the target gas or detect a gas other than hydrogen gas.

The substrate 141 can be a glass substrate having a thickness of approximately 0.5 mm (500 µm). The laminate film 142 is formed by laminating a reflective metal layer 424, a dielectric optical interference layer 423, a magnetic metal layer 422, a gas sensing layer 421 in order from the bottom to the top. Another dielectric optical interference layer can be interposed between the magnetic metal layer 422 and the gas sensing layer 421. As will be described later, the thicknesses of the individual layers are determined appropriately so that the light that has entered the laminate film 142 will be multiply reflected within the laminate film 142. For example, the thicknesses of the layers are approximately several-tens nanometers. The laminate film 142 can have a different configuration that causes effects described later, instead of the configuration illustrated in FIG. 2.

The gas sensing layer 421 changes in optical characteristics such as refractive index and absorption coefficient because of reaction to hydrogen gas. Hydrogen gas can be detected by measuring the characteristics change of the reflected light caused by the change in optical characteristics of the gas sensing layer 421. The gas sensing layer 421 can be made of any material that changes in optical characteristics such as refractive index and absorption coefficient because of reaction to hydrogen gas. For example, Pd can be employed because Pd exhibits significant optical change in response to contact to hydrogen gas.

The magnetic metal layer 422 can be a monolayer film or a multilayer film of common magnetic material. The magnetic material can be a metal such as Fe, Co, or Ni or an alloy thereof. The dielectric optical interference layer 423 can be made of an oxide or a nitride that is transparent for a specific wavelength of light, such as $SiO_2$, ZnO, MgO, $TiO_2$, or AlN. The material of the reflective metal layer 424 can be a common metallic material such as Ag, Al, Au, Cu or an alloy thereof having high reflectance to the specific wavelength of light emitted from the light source 11.

The mechanism of detecting hydrogen gas with the gas sensing apparatus 1 is described. The laminate film 142 is configured so that the multiple reflection within the laminate film 142 changes the polarization angle of the reflected light therefrom maximally relative to the linearly polarized incoming light having a specific wavelength.

The gas sensing apparatus 1 illuminates the laminate film 142 with linearly polarized light while making the magnetic field applicator 18 apply a magnetic field strong enough to saturate the magnetization of the magnetic metal layer 422 in one direction to the laminate film 142. The illuminating light (incoming light) is reflected multiple times within the laminate film 142 to receive significant magneto-optic effect and as a result, the reflected light goes out with a polarization angle much different from that of the incoming light.

When the gas sensing layer 421 is in contact with hydrogen gas, an optical characteristic such as refractive index or absorption coefficient changes in the gas sensing layer 421. For this reason, the optical interference condition in the laminate film 142 changes, so that the effect of multiple reflection diminishes. When this action occurs under the condition where a magnetic field is being applied, the frequency of the change in polarization angle caused by the magneto-optic effect occurring in the magnetic metal layer 422 decreases and as a result, the change in polarization angle of the outgoing light relative to the polarization angle of the linearly polarized incoming light becomes small, compared to the case where hydrogen gas does not exist.

The polarization angle of the light reflected off the laminate film 142 varies depending on the orientation of magnetization of the magnetic metal layer 422 of the laminate film 142. The gas sensing apparatus 1 applies a magnetic field cyclically changing its direction to opposite to the laminate film 142 with the magnetic field applicator 18 and detects the change of the polarization angle in the light reflected off the laminate film 142 to detect hydrogen gas with high accuracy.

Since the second polarizer 16 transmits only the light (component) polarized linearly in a specific direction, the intensity of the light transmitted through the second polarizer 16 out of the reflected light off the laminate film 142 changes depending on the polarization angle of the reflected light off the laminate film 142. The photodetector 17 detects the change in polarization angle in the form of change in the intensity of light.

The gas sensing apparatus 1 can measure the change in magneto-optic effect of the laminate film 142 caused by hydrogen gas in a different way. For example, detecting the polarization angle with a photodetector like differential detection using a polarized beam splitter can be employed. In that case, the second polarizer 16 can be eliminated. In another example, the gas sensing apparatus 1 can apply a fixed (non-alternating) magnetic field to the laminate film 142 in detecting the target gas. The gas sensing apparatus 1 can also utilize transversal Kerr effect. The transversal Kerr effect occurs when the direction of the applied magnetic field is within the plane of the laminate film 142 and perpendicular to the projection of the incoming light and the reflected light on the reflection surface. The change of the transversal Kerr effect is observed not in polarization angle but in reflectance (the intensity of the reflected light). Accordingly, the second polarizer 16 can be eliminated. The second polarizer 16 can be replaced by a wavelength filter.

Figure 3A:
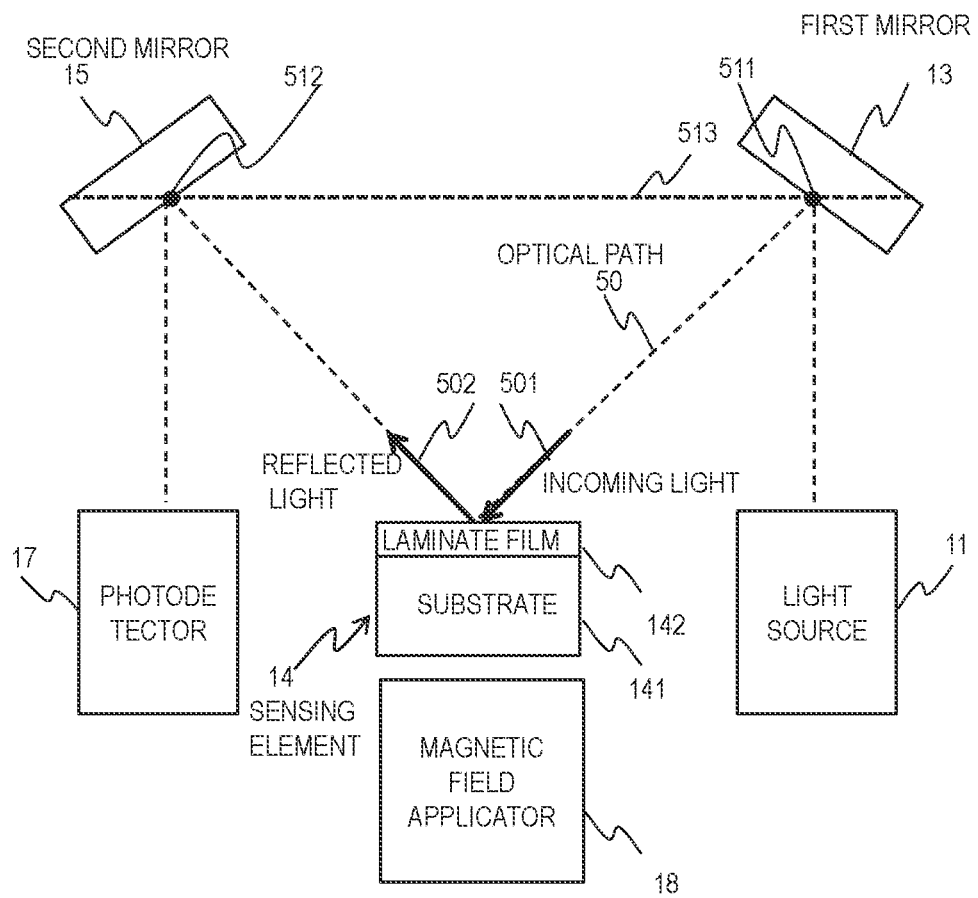
FIG. 3A illustrates positional relations of components to a plane defined by the optical path in Embodiment 1.

FIG. 3A illustrates positional relations of components of the gas sensing apparatus 1 to a plane (virtual plane) defined by the optical path 50 of the gas sensing apparatus 1. The light on the optical path 50 hits a point 511 on the first mirror 13 and is reflected. The point 511 is a point where the light goes out from the first mirror 13. The light on the optical path 50 hits a point 512 on the second mirror 15 and is reflected. The point 512 is a point where the light enters the second mirror 15.

The incidence plane of the incoming light 501 to the sensing face of the gas sensing element 14 and the reflected light 502 therefrom is a plane including the incoming light 501 and the reflected light 502. In the example of FIG. 3A, the normal to this incidence plane is perpendicular to the sheet of the drawing. A virtual plane 513 including the above-described pointes 511 and 512 and being perpendicular to the incidence plane of the incoming light 501 and the reflected light 502 can be defined. Hereinafter, the term "virtual plane" is occasionally abbreviated as "plane". In the example of FIG. 3A, the plane 513 is perpendicular to the sheet of the drawing. The gas sensing element 14, the light source 11, the photodetector 17, and the magnetic field applicator 18 are disposed on the same side (on the lower side of FIG. 3A) with respect to the plane 513. This disposition simplifies the configuration in front of the sensing face of the sensing element to facilitate the exposure of the sensing face of the gas sensing element to the atmosphere to be examined and reduce the restriction for the installation of the gas sensing apparatus.

Figure 3B:
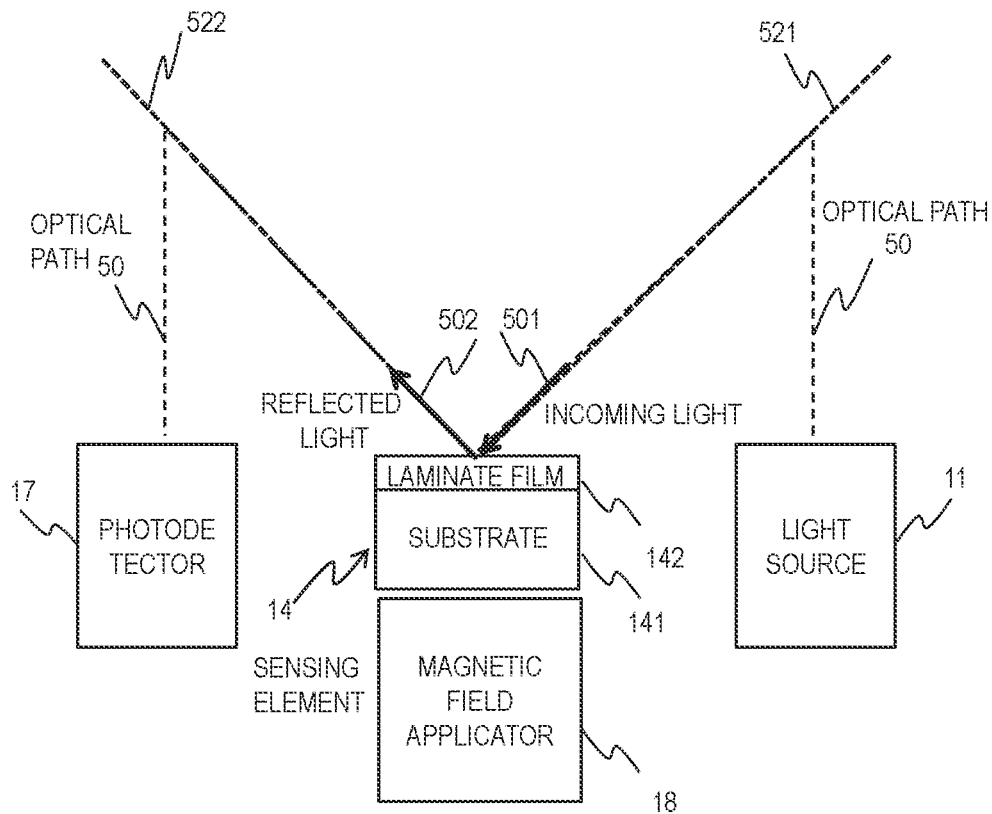
FIG. 3B illustrates positional relations of components to other planes defined by the optical path in Embodiment 1.

FIG. 3B illustrates positional relations of components of the gas sensing apparatus 1 to other planes (virtual planes) defined by the optical path 50 of the gas sensing apparatus 1. The plane 521 includes the incoming light 501 and is perpendicular to the incidence plane of the incoming light 501 and the reflected light 502; one end of the plane 521 is defined by the sensing face of the gas sensing element 14. The plane 522 includes the reflected light 502 and is perpendicular to the incidence plane of the incoming light 501 and the reflected light 502; one end of the plane 522 is defined by the sensing face of the gas sensing element 14. These ends on the sensing face are common to the plane 521 and the plane 522.

In the example of FIG. 3B, the gas sensing element 14, the light source 11, the photodetector 17, and the magnetic field applicator 18 are disposed on the same side (on the lower side of FIG. 3B) with respect to the planes 521 and 522. This disposition simplifies the configuration in front of the sensing face of the sensing element to facilitate the exposure of the sensing face of the gas sensing element to the atmosphere to be examined and reduce the restriction for the installation of the gas sensing apparatus.

Figure 3C:
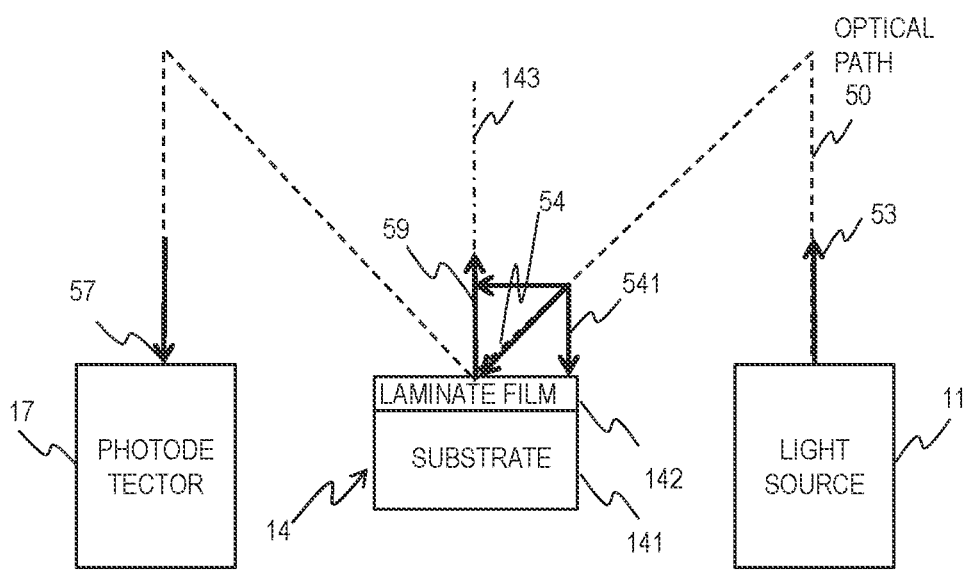
FIG. 3C illustrates disposition of a light source, a gas sensing element, and a photodetector together with the directions of light incoming to and going out from these components in Embodiment 1.

FIG. 3C illustrates disposition of the light source 11, the gas sensing element 14, and the photodetector 17 together with the direction and orientation (the sense of a vector) of the light incoming to and going out from these components. The direction and orientation of light is expressed by a directional vector. First, a normal vector 59 to the sensing face directed from the sensing face to the atmosphere to be examined is defined along the normal 143 that is perpendicular to the sensing face of the gas sensing element 14 as a reference for the orientation of light. The directional vector 54 of the incoming light to the gas sensing element 14 has a component 541 parallel to the normal vector 59 to the sensing face. The directional vector 54 of the incoming light has also a component perpendicular to the normal vector 59 to the sensing face (the light is obliquely incoming and obliquely reflected).

The directional vector 53 of the light emitted from the light source 11 has a component parallel to the normal vector 59 to the sensing face. In this example, the directional vector 53 is parallel to the normal vector 59 to the sensing face and does not have a component perpendicular to the normal vector 59 to the sensing face. The directional vector 53 has the same orientation as the normal vector 59 to the sensing face.

The directional vector 57 of the light entering the photodetector 17 has a component parallel to the normal vector 59 to the sensing face. In this example, the directional vector 57 is parallel to the normal vector 59 to the sensing face and does not have a component perpendicular to the normal vector 59 to the sensing face. The directional vector 57 has the orientation opposite to the normal vector 59 to the sensing face.

As described with reference to FIG. 1, the first mirror 13 and the second mirror 15 bend the optical path 50 between the light source 11 and the photodetector 17. As a result, the relation of the vectors described with reference to FIG. 3C is attained. The three directional vectors 53, 54, and 57 having the above-described relation enable the disposition of the light source 11 and the photodetector 17 on the same side as the gas sensing element 14, instead of the disposition such that the light source 11 and the photodetector 17 are on the opposite side of the sensing element 14 across the atmosphere 30 to be examined.

Specifically, the light source 11 and the photodetector 17 are disposed on the substrate side of the gas sensing element 14 with respect to the space of the atmosphere 30 that may include the target gas. Further in the configuration example of FIG. 1, the light source 11, the photodetector 17, the gas sensing element 14, and the magnetic field applicator 18 are disposed on the same one side with respect to the atmosphere 30.

The gas sensing apparatus 1 illuminates the gas sensing element 14 from the atmosphere side with measuring light that is emitted from the substrate side of the gas sensing element 14 toward the laminate film side and reflected by the first mirror 13. The reflected light from the gas sensing element 14 toward the atmosphere is reflected by the second mirror 15 and directed to the photodetector 17. This configuration contributes to providing an open space in front of the laminate film 142 of the gas sensing element 14.

In the configuration example of FIG. 1, when the gas sensing element 14 is seen along the normal 143 from the film side of the laminate film 142, neither the light source 11 nor the photodetector 17 overlap the gas sensing element 14. This disposition provides an open space in front of the laminate film 142 so that the laminate film 142 is more appropriately exposed to the atmosphere 30 to be examined.

In the configuration example of FIG. 1, the directional vector 53 of the light emitted from the light source 11 and the directional vector 57 of the light entering the photodetector 17 are parallel to the normal 143 to the laminate film 142; however, these vectors can have components parallel to and perpendicular to the normal 143. For example, the vector 53 has a component parallel to the normal 143 larger than the component perpendicular to the normal 143 and the vector 57 also has a component parallel to the normal 143 larger than the component perpendicular to the normal 143.

In the configuration example of FIG. 1, the light emitting face (the top face in FIG. 1) of the light source 11 and the entrance face (the top face in FIG. 1) of the photodetector 17 are located closer to the atmosphere 30 (upper in FIG. 1) than the exposed sensing face (film surface) of the laminate film 142. In another example, either the light emitting face of the light source 11 or the entrance face of the photodetector 17 can be located lower than the sensing face of the laminate film 142 in FIG. 1 or located farther from the atmosphere 30.

Figure 4:
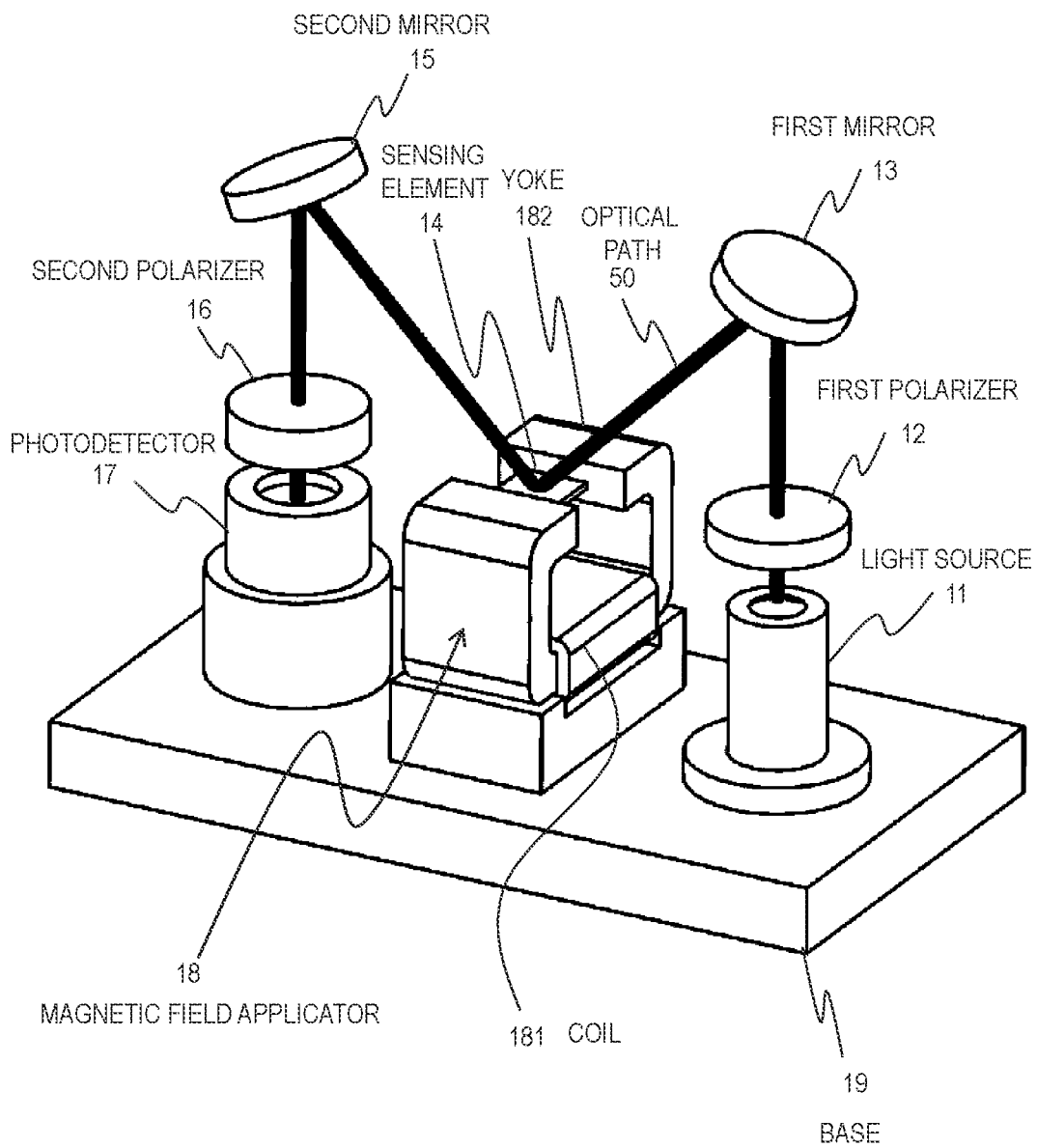
FIG. 4 illustrates a more specific configuration example of the gas sensing apparatus in Embodiment 1.

FIG. 4 illustrates a more specific configuration example of the gas sensing apparatus 1. In the configuration example illustrated in FIG. 4, the light source 11, the photodetector 17, and the magnetic field applicator 18 are fixed to a base 19. The first polarizer 12, the first mirror 13, the second mirror 15, and the second polarizer 16 are held by not-shown components fixed to the base 19. The first polarizer 12 can be attached on the front of the light source 11 and the second polarizer 16 can be attached on the front of the photodetector 17. Because of these structures, these components are fixed in position and orientation to define the optical path 50 and be unified into the gas sensing apparatus 1. In practical use, the user installs this unified gas sensing apparatus 1 at a desired place.

The magnetic field applicator 18 includes a coil 181, which is a magnetic field generating element for generating a magnetic field, and a yoke 182 for directing the magnetic field generated by the coil 181 to the gas sensing element 14. The coil 181 is wound around the yoke 182 and the gas sensing element 14 is disposed within the gap between the magnetic poles of the yoke 182. The yoke 182 is fixed to the base 19 with a mount interposed therebetween. The base 19 in this example has a plate-like shape but the shape is not limited to this example.

In the configuration example of FIG. 4, the gas sensing element 14 and the magnetic field applicator 18 are located between the light source 11 and the photodetector 17 when seen in the direction normal to the sensing face of the gas sensing element 14. When seen in the same direction, the gas sensing element 14 is inside of the magnetic field applicator 18. The underside (bottom face) of the magnetic field applicator 18 is closer to the base 19 than the underside of the gas sensing element 14. The magnetic field applicator 18 is located between the light source 11 and the photodetector 17 when seen perpendicularly to the plane (reflection surface) including incoming light and reflected light to and from the film surface of the gas sensing element 14.

In the configuration example of FIG. 4, the magnetic field applicator 18 applies a magnetic field in the direction along the sensing face (principal surface) of the laminate film 142.

The magnetic field applicator 18 including a coil 181 and a yoke 182 can easily control the intensity of the magnetic field and efficiently apply the magnetic field to the laminate film 142. The magnetic field applicator 18 can be configured differently; for example, it can employ a hard magnetic material or a hollow coil to surround the gas sensing element 14.

As described above, the components of the gas sensing apparatus 1 in this embodiment are disposed so that the components in need of electric wiring, or the components other than the first mirror 13 and the second mirror 15, are gathered around the base 19; the structure around the sensing face of the laminate film 142 of the gas sensing element 14 is simplified. Accordingly, the sensing face is easily exposed to the atmosphere 30 to be examined with small limitation for its installation to detect a gas.

Embodiment 2

Embodiment 1 includes a first mirror 13 as a first optical element for bending the optical path 50 and a second mirror 15 as a second optical element for bending the optical path 50. Embodiment 2 described hereinafter employs optical fibers as the first and the second optical elements for bending the optical path 50. Optical fibers increase the flexibility in forming the optical path 50.

Figure 5A:
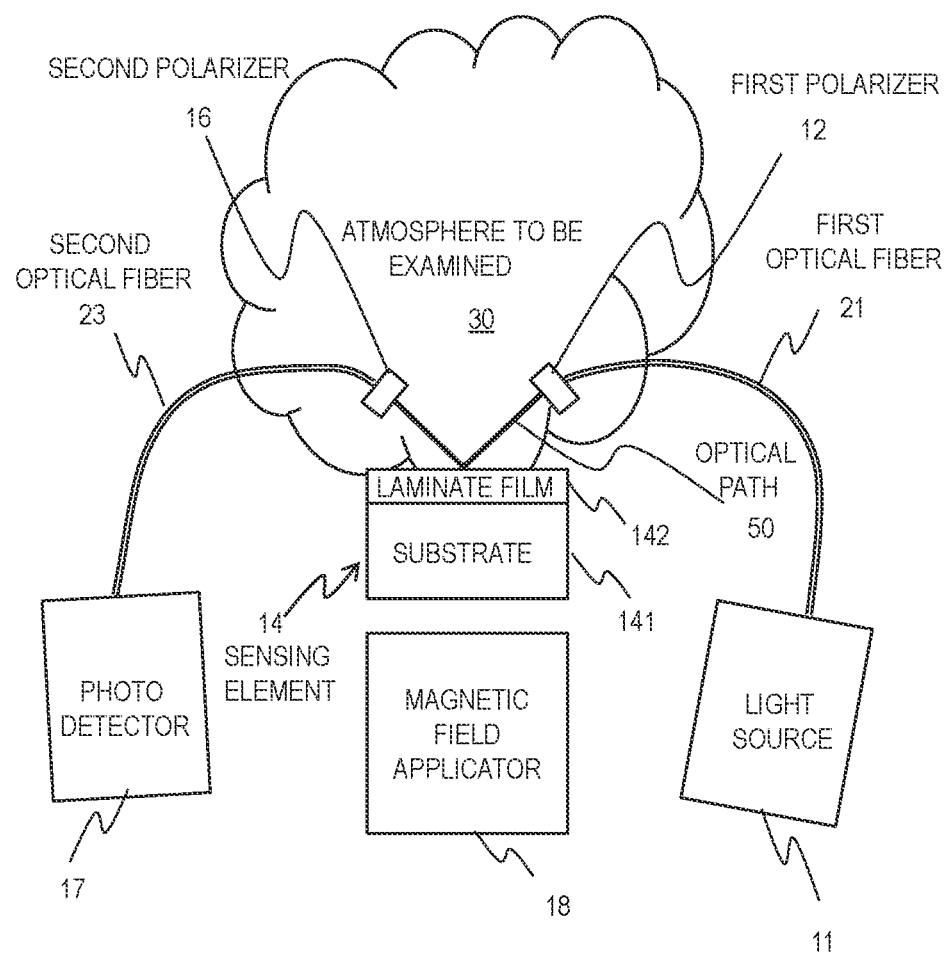
FIG. 5A schematically illustrates a configuration example of a gas sensing apparatus in Embodiment 2.

FIG. 5A schematically illustrates a configuration example of the gas sensing apparatus 1 in this embodiment. Differences from Embodiment 1 are mainly described. The first optical fiber 21 is disposed between the light source 11 and the first polarizer 12 on the optical path 50. The second optical fiber 23 is disposed between the second polarizer 16 and the photodetector 17 on the optical path 50. A part of the optical path 50 is in the first optical fiber 21 and another part of the optical path 50 is in the second optical fiber 23. Each of the first optical fiber 21 and the second optical fiber 23 bends the optical path 50.

The optical fibers 21 and 23 enables the light source 11, the photodetector 17, the gas sensing element 14, and the magnetic field applicator 18 to be disposed on the same one side of the atmosphere 30 to be examined. The light from the light source 11 passes through the first optical fiber 21 and enters the first polarizer 12. The linearly polarized light from the first polarizer 12 enters the laminate film 142 and the reflected light therefrom enters the second polarizer 16. The light transmitted through the second polarizer 16 passes through the second optical fiber 23 and enters the photodetector 17.

Figure 5B:
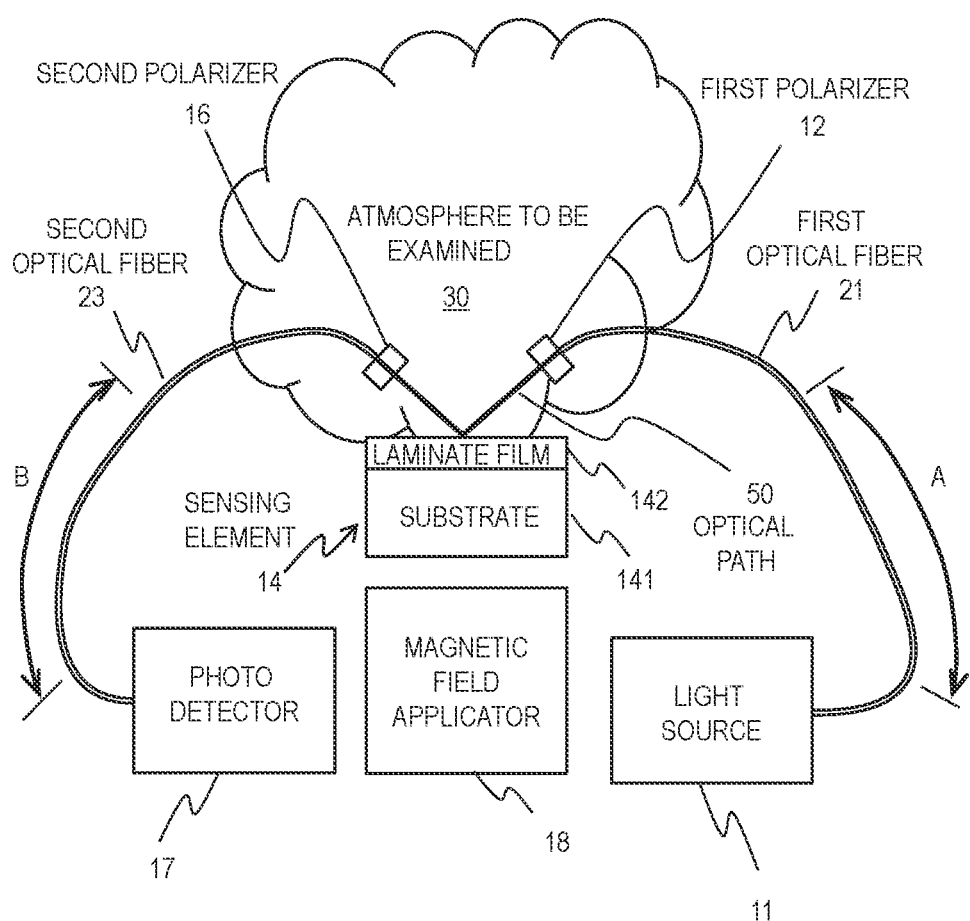
FIG. 5B schematically illustrates another configuration example of a gas sensing apparatus in Embodiment 2.

FIG. 5A illustrates an embodiment in which the light source 11 and the photodetector 17 are disposed at places close to their places in FIG. 1. However, various configurations are available as far as the above-described conditions are satisfied in the route where the optical fibers 21 and 23 are laid. FIG. 5B schematically illustrates another configuration example of the gas sensing apparatus 1 in Embodiment 2. As illustrated in FIG. 5B, the optical fibers can be elongated to attain a configuration such that the light source 11 emits light in the lateral direction or the light enters the photodetector 17 in the lateral direction and another configuration such that the light source 11 and the photodetector 17 are placed considerably distant from the gas sensing element 14.

Figure 6A:
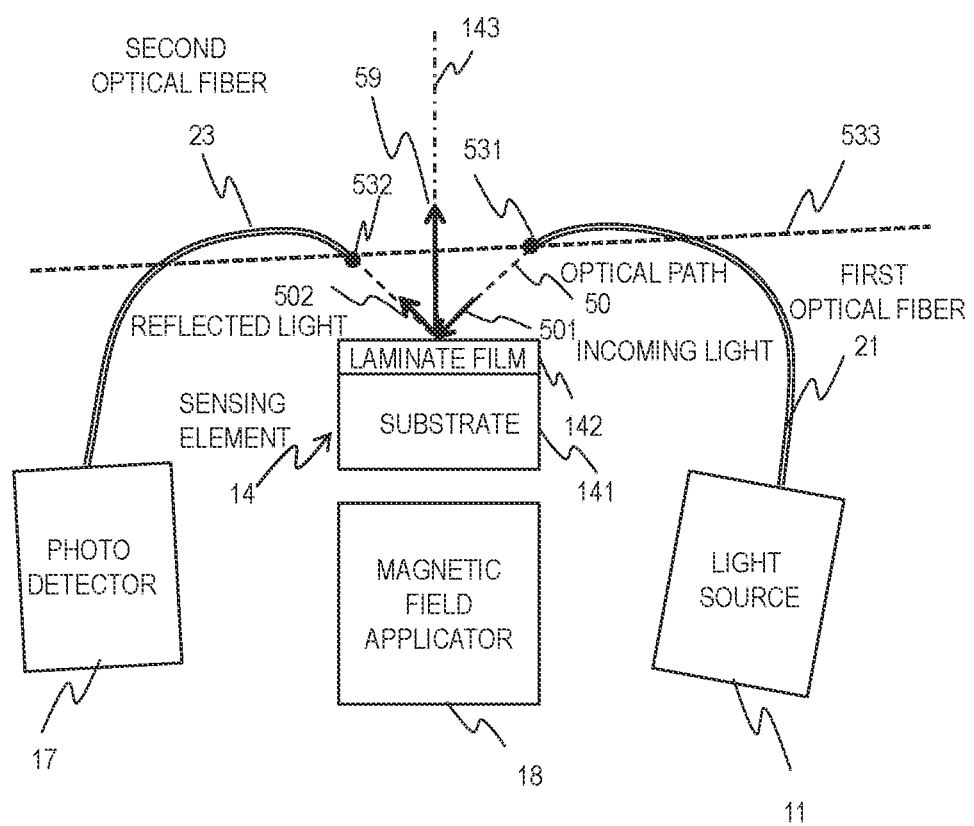
FIG. 6A illustrates positional relations of components to a plane defined by the optical path in Embodiment 2.

FIG. 6A illustrates positional relations of components of the gas sensing apparatus to a plane (virtual plane) defined by the optical path 50 of the gas sensing apparatus 1. The point 531 is a point where the light goes out from the first optical fiber 21. The point 532 is a point where the light enters the second optical fiber 23.

A virtual plane 533 including the above-described points 531 and 532 and being perpendicular to the incidence plane of the incoming light 501 and the reflected light 502 can be defined. In the example of FIG. 6A, the plane 533 is perpendicular to the sheet of the drawing. The gas sensing element 14, the light source 11, the photodetector 17, and the magnetic field applicator 18 are disposed on the same side (on the lower side of FIG. 6A) with respect to the plane 533. This disposition simplifies the configuration in front of the sensing face of the sensing element to facilitate the exposure of the sensing face of the gas sensing element to the atmosphere to be examined and reduce the restriction for the installation of the gas sensing apparatus.

Figure 6B:
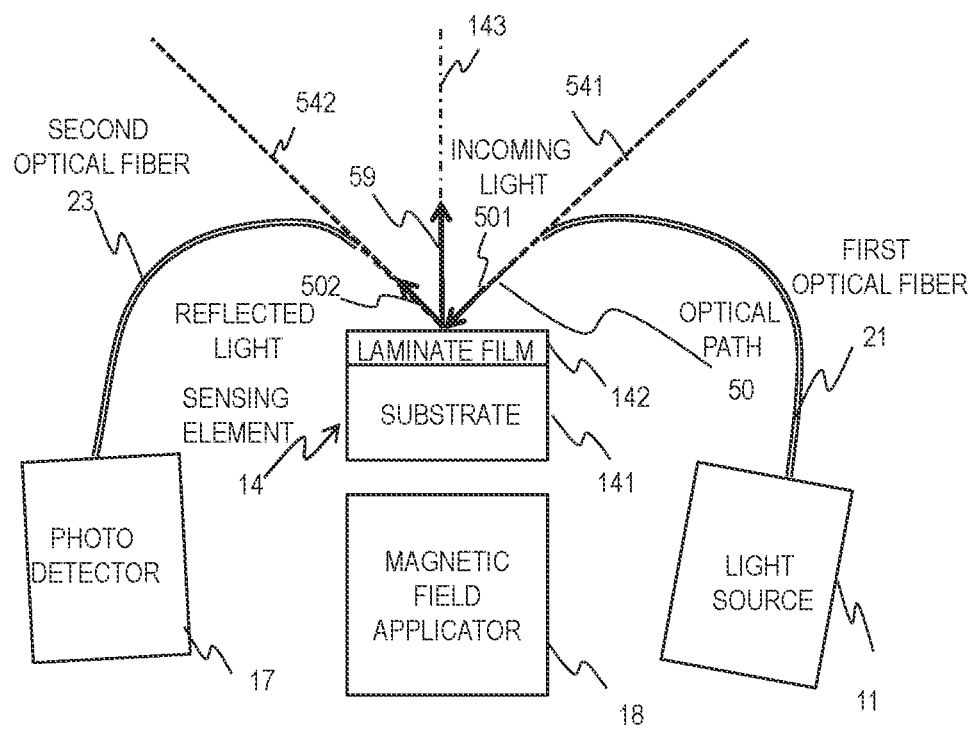
FIG. 6B illustrates positional relations of components to other planes defined by the optical path in Embodiment 2.

FIG. 6B illustrates positional relations of components of the gas sensing apparatus 1 to other planes (virtual planes) defined by the optical path 50 of the gas sensing apparatus 1. The plane 541 includes the incoming light 501 and is perpendicular to the incidence plane of the incoming light 501 and the reflected light 502; one end of the plane 541 is defined by the sensing face of the gas sensing element 14. The plane 542 includes the reflected light 502 and is perpendicular to the incidence plane of the incoming light 501 and the reflected light 502; one end of the plane 542 is defined by the sensing face of the gas sensing element 14. These ends on the sensing face are common to the plane 541 and the plane 542.

In the example of FIG. 6B, the gas sensing element 14, the light source 11, the photodetector 17, and the magnetic field applicator 18 are disposed on the same side (on the lower side of FIG. 6B) with respect to the planes 541 and 542. This disposition simplifies the configuration in front of the sensing face of the sensing element to facilitate the exposure of the sensing face of the gas sensing element to the atmosphere to be examined and reduce the restriction for the installation of the gas sensing apparatus. The description provided with reference to FIGS. 6A and 6B is applicable to the configuration example illustrated in FIG. 5B.

Figure 6C:
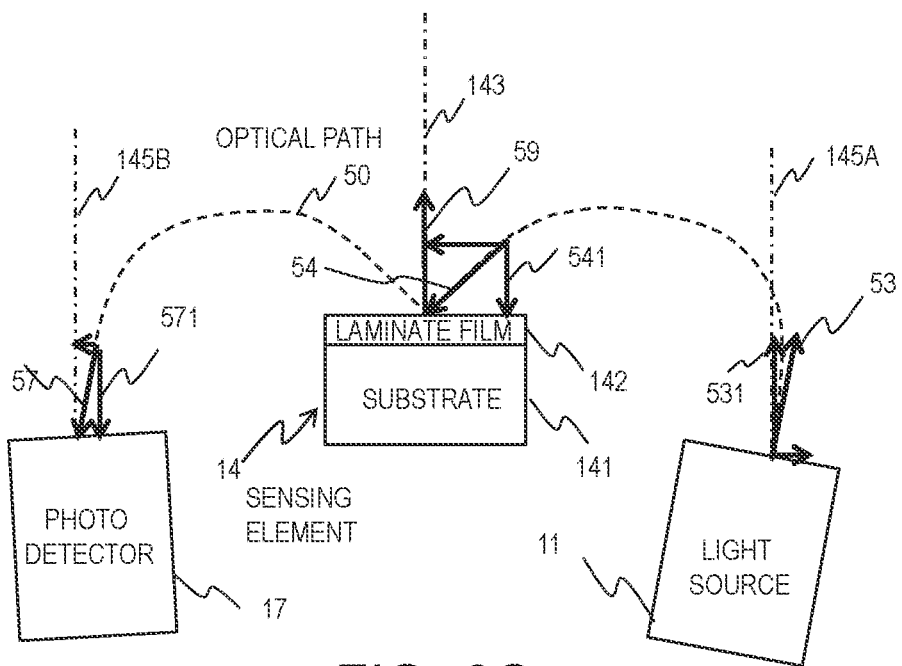
FIG. 6C illustrates disposition of a light source, a gas sensing element, and a photodetector together with the directions of light incoming to and going out from these components in Embodiment 2.

FIG. 6C illustrates disposition of the light source 11, the gas sensing element 14, and the photodetector 17 together with the direction and orientation (the sense of a vector) of the light incoming to and going out from these components. The direction and orientation of light is expressed by a directional vector. In FIG. 6C, too, a normal vector 59 to the sensing face is defined as a reference for the orientation of light. The directional vector 54 of the incoming light to the gas sensing element 14 has a component 541 parallel to the normal vector 59 to the sensing face. The directional vector 54 of the incoming light also has a component perpendicular to the normal vector 59 to the sensing face (the light is obliquely incoming and obliquely reflected). In FIG. 6C, the dashed-dotted lines 145A and 145B are parallel to the normal 143.

The directional vector 53 of the light emitted from the light source 11 has a component 531 parallel to the normal vector 59 to the sensing face. The directional vector 53 also has a component perpendicular to the normal vector 59 to the sensing face. The orientation of the component 531 of the directional vector 53 that is parallel to the normal vector 59 to the sensing face is the same as the orientation of the normal vector 59 to the sensing face. The component 531 parallel to the normal vector 59 to the sensing face is larger than the component perpendicular to the normal vector 59 to the sensing face.

The directional vector 57 of the light entering the photodetector 17 has a component 571 parallel to the normal vector 59 to the sensing face. In this example, the directional vector 57 also has a component perpendicular to the normal vector 59 to the sensing face. The orientation of the component 571 of the directional vector 57 that is parallel to the normal vector 59 to the sensing face is opposite to the orientation of the normal vector 59 to the sensing face. The component 571 parallel to the normal vector 59 to the sensing face is larger than the component perpendicular to the normal vector 59 to the sensing face.

As described with reference to FIG. 5A, the first optical fiber 21 and the second optical fiber 23 bend the optical path 50 between the light source 11 and the photodetector 17. As a result, the relation of the vectors described with reference to FIG. 6C is attained. The three directional vectors 53, 54, and 57 having the above-described relation enable the disposition of the light source 11 and the photodetector 17 on the same side as the gas sensing element 14, instead of the disposition such that the light source 11 and the photodetector 17 are on the opposite side of the sensing element 14 across the atmosphere 30 to be examined.

Unlike the disposition in FIG. 5A, the relation described with reference to FIG. 6C does not apply to the directional vectors of the light outgoing from the light source 11 and the light entering the photodetector 17 in the disposition in FIG. 5B where the first optical fiber 21 and the second optical fiber 23 are elongated. However, the first optical fiber 21 forming the optical path from the light source 11 to the first polarizer 12 and the second optical fiber 23 forming the optical path from the second polarizer 16 to the photodetector 17 have at least one section where the tangent vector along the optical path satisfies the relation described with reference to FIG. 6C, like the section A and the section B (see FIG. 5B).

As understood from the above, there is a directional vector of a light ray including a component parallel to and in the same orientation as the normal vector 59 to the sensing face of the gas sensing element 14 in the section from the point where a light ray goes out from the light source 11 to the point where the light ray goes out from the first optical fiber 21. The incoming light to the sensing face of the gas sensing element 14 has a component parallel to and in the opposite orientation to the normal vector 59. Further, there is a directional vector of a light ray including a component parallel to and in the opposite orientation to the normal vector 59 to the sensing face of the gas sensing element 14 in the section from the point where a light ray enters the second optical fiber 23 to the point where the light ray enters the photodetector 17. This configuration applies to the configurations illustrated in FIGS. 5A and 5B including a first mirror 13 and a second mirror 15 in place of the first optical fiber 21 and the second optical fiber 23.

When optical fibers are laid in a route including the above-described sections, disposition of the light source 11 and the photodetector 17 on the same side as the gas sensing element 14 becomes available instead of disposition such that the light source 11 and the photodetector 17 are on the opposite side of the sensing element 14 across the atmosphere 30 to be examined and further, the flexibility in disposition of the light source 11 and the photodetector 17 increases in the gas sensing apparatus 1.

The above-described configuration that illuminates the gas sensing element 14 by the first optical fiber 21 from the atmosphere side and takes the reflected light into the second optical fiber 23 to guide the light to the photodetector 17 allows the structure in front of the surface (sensing face) of the laminate film 142 to be simplified more than the configuration in Embodiment 1 including mirrors and facilitates exposure of the laminate film 142 to the atmosphere 30 to be examined. Employment of optical fibers reduces the restriction for the disposition of the light source 11 and the photodetector 17 and increases the flexibility in designing the gas sensing apparatus 1. Reducing the height of the gas sensing apparatus 1 significantly reduces the restriction for installation of the gas sensing apparatus 1. Either one of the two optical fibers can be replaced by a mirror.

Embodiment 3

The gas sensing apparatus described hereinafter has components to be electrified within a container. When the target gas is a combustible or explosive gas such as hydrogen, isolating the components to be electrified from the atmosphere to be examined increases the safety.

Figure 7:
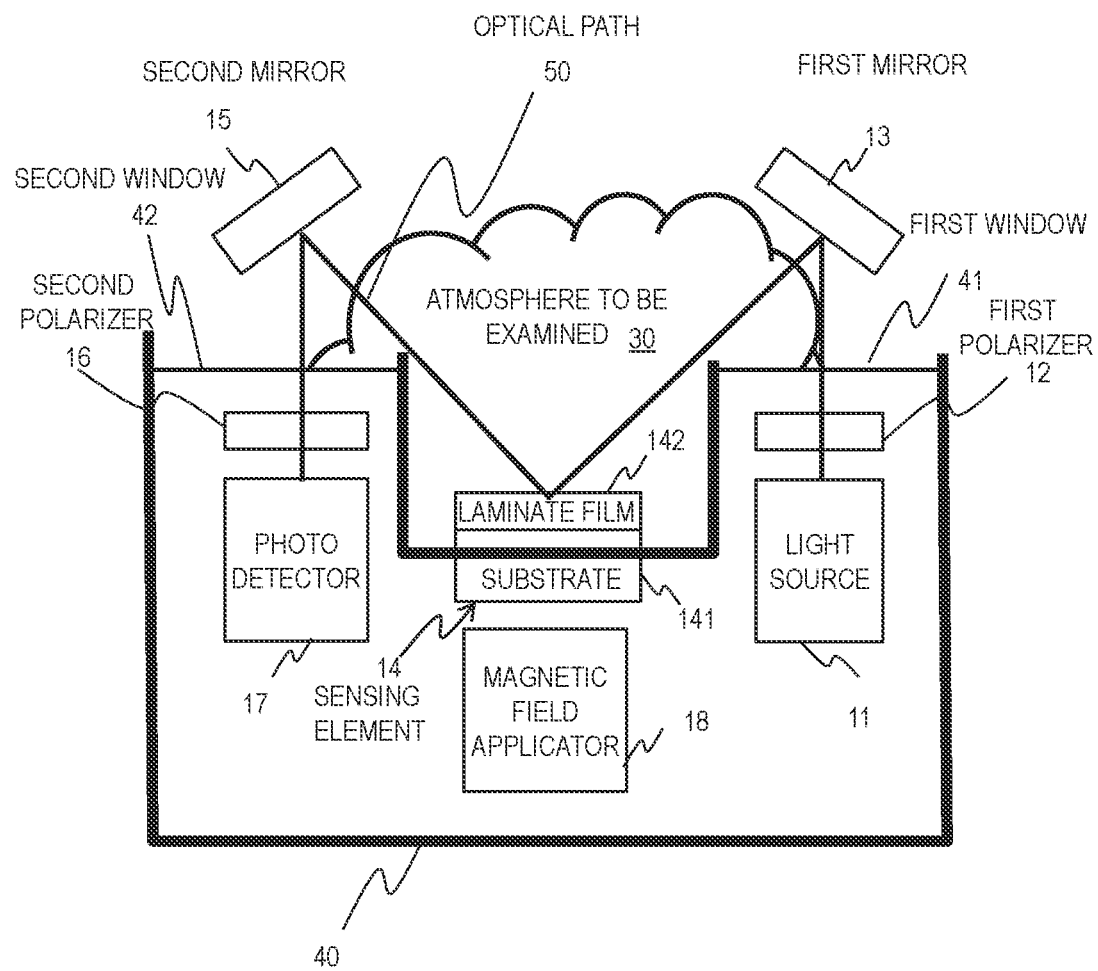
FIG. 7 illustrates a configuration example of an explosion-proof gas sensing apparatus in Embodiment 3.

FIG. 7 illustrates a configuration example of an explosion-proof gas sensing apparatus 1. Differences from the configuration example in Embodiment 1 illustrated in FIG. 1 are mainly described. The gas sensing apparatus 1 includes an air-tight container 40. The container 40 can be made of resin or metal. The container 40 accommodates the light source 11, the photodetector 17, and the magnetic-field applicator 18. These are components to be electrified (active components). The container 40 further accommodates the first polarizer 12 and the second polarizer 16. These are components not to be electrified; they can be disposed outside the container 40. The first mirror 13 and the second mirror 15 are components not to be electrified; they are disposed outside the container 40.

The gas sensing element 14 is fixed to the container 40 in such a manner that the laminate film 142 will be exposed to the atmosphere 30 to be examined. In the configuration example of FIG. 7, the substrate 141 of the gas sensing element 14 is fitted in an opening (not shown) provided in the container 40; a part of the substrate 141 is inside the container 40 and the remaining is exposed to the outside of the container 40. The container 40 can be made of a material that transmits magnetic flux. In that case, the entire gas sensing element 14 can be disposed outside the container 40 so that the magnetic field applicator 18 applies a magnetic field to the gas sensing element 14 from behind the container 40.

The container 40 has a first window 41 and a second window 42. The first window 41 and the second window 42 are transparent to the measuring light having a specific wavelength. The first window 41 is provided on the optical path 50, between the light source 11 and the first mirror 13, more specifically, between the first polarizer 12 and the first mirror 13. The second window 42 is provided on the optical path 50, between the second mirror 15 and the photodetector 17, more specifically, between the second mirror 15 and the second polarizer 16.

The configuration in FIG. 7 achieves isolation of the light source 11, the photodetector 17, and the magnetic field applicator 18 of components to be electrified from the atmosphere 30 to be examined while maintaining the sensing function of the gas sensing apparatus 1. In this configuration example, the light source 11, the photodetector 17, the gas sensing element 14, and the magnetic field applicator 18 are disposed on the same one side of the atmosphere 30 to be examined as described in Embodiment 1; accordingly, one airtight container (airtight chamber) 40 having a simple shape can accommodate the above-described components, allowing the laminate film 142 of the gas sensing element 14 to be exposed to the atmosphere 30 to be examined.

Figure 8:
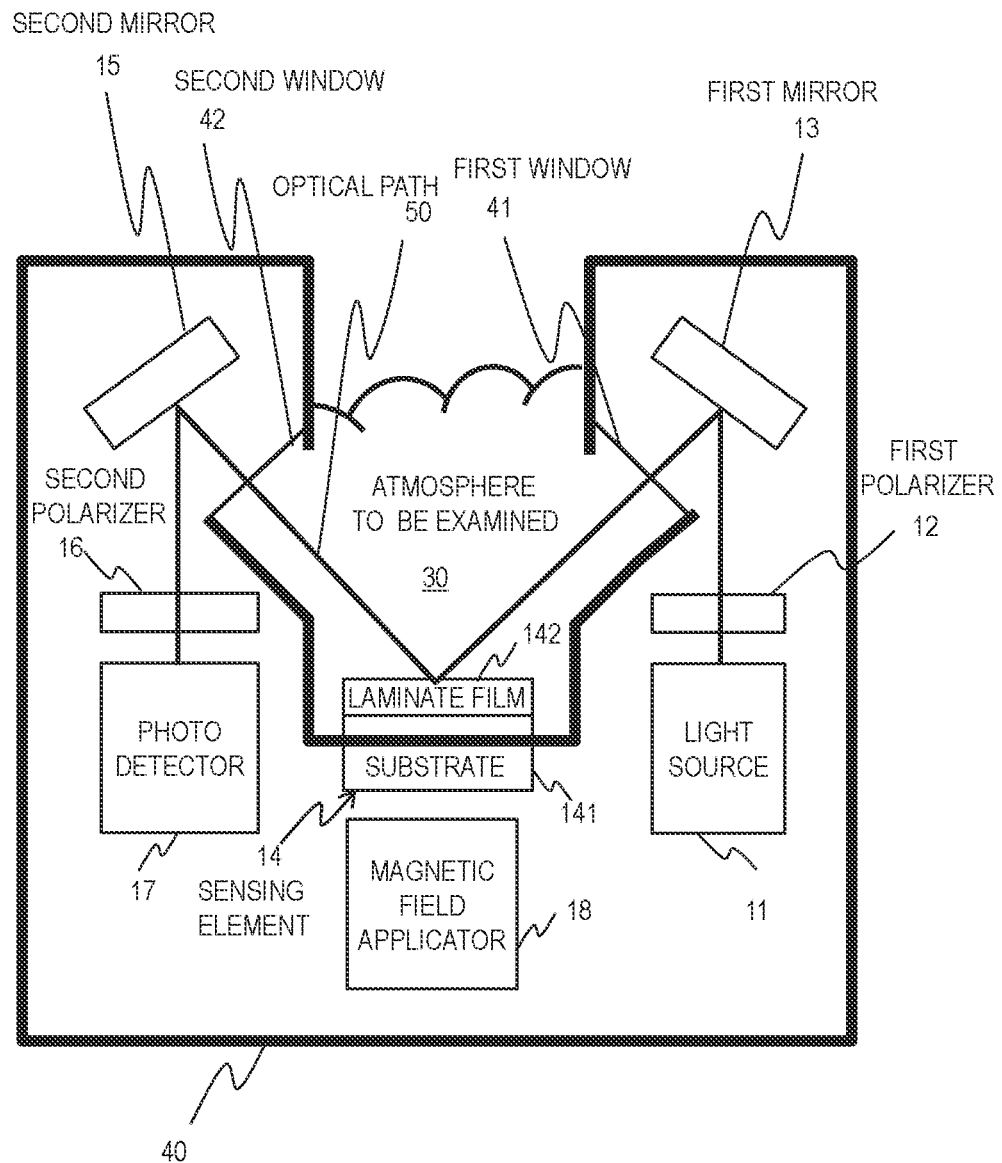
FIG. 8 illustrates another configuration example of an explosion-proof gas sensing apparatus in Embodiment 3.

FIG. 8 illustrates another configuration example of an explosion-proof gas sensing apparatus 1. The airtight container 40 accommodates the first mirror 13 and the second mirror 15 in addition to the components accommodated in the container 40 in the configuration example of FIG. 7. This configuration protects the reflection surfaces of the first mirror 13 and the second mirror 15 from contamination while maintaining the ease of installation of the explosion-proof gas sensing apparatus 1.

Figure 9:
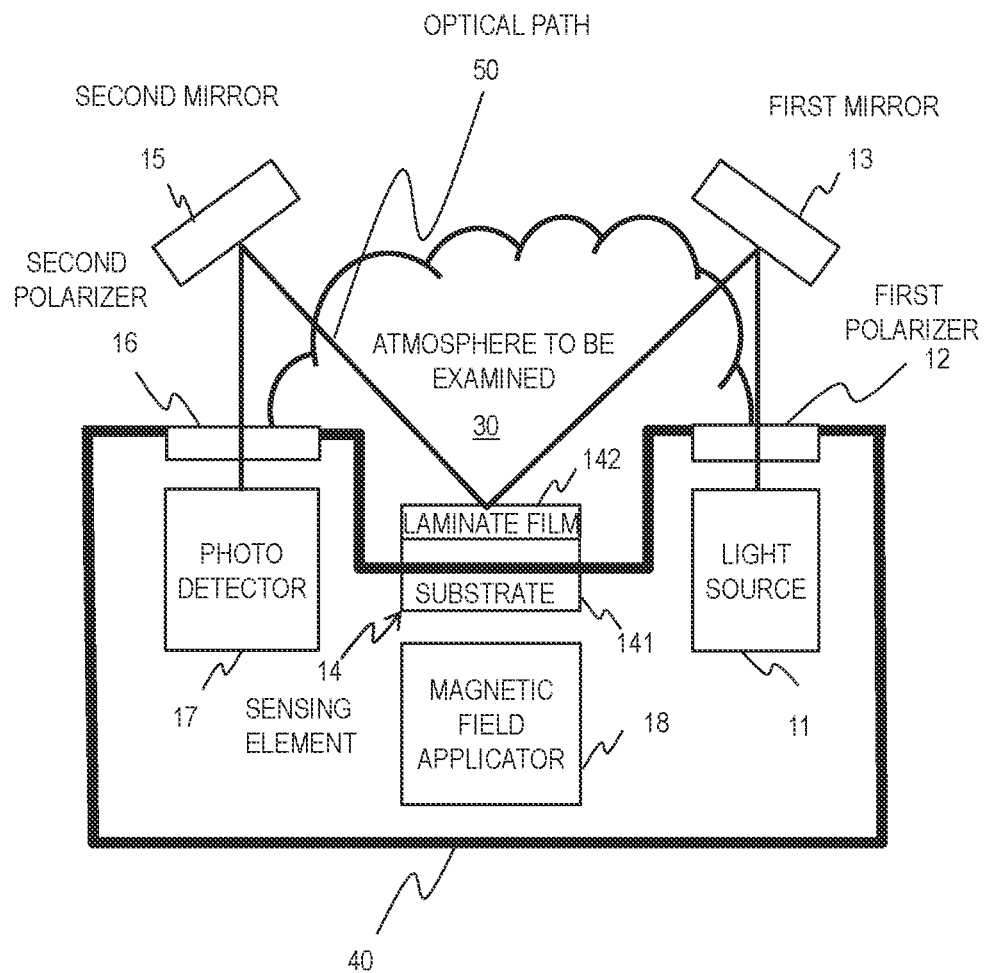
FIG. 9 illustrates still another configuration example of an explosion-proof gas sensing apparatus in Embodiment 3.

FIG. 9 illustrates still another configuration example of an explosion-proof gas sensing apparatus 1. Differences from the configuration example of FIG. 7 are mainly described. The windows of the airtight container 40 have another additional function. Specifically, the first polarizer 12 and the second polarizer 16 are fitted in the openings of the airtight container 40 to form windows. The first polarizer 12 replaces the first window 41 in the configuration example of FIG. 7 and the second polarizer 16 replaces the second window 42. This configuration example achieves reduction in the number of components.

Figure 10:
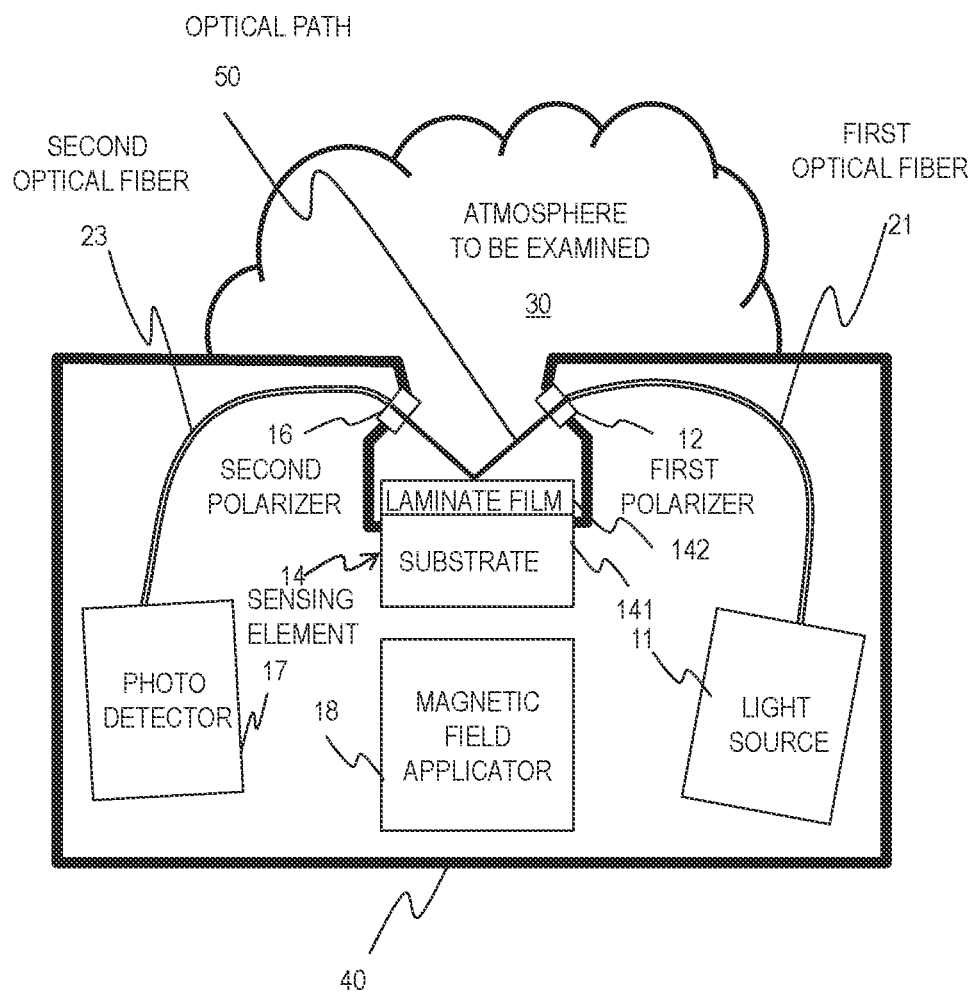
FIG. 10 illustrates still another configuration example of an explosion-proof gas sensing apparatus in Embodiment 3.

FIG. 10 illustrates still another configuration example of an explosion-proof gas sensing apparatus 1. Differences from the configuration examples of FIGS. 5A and 5B are mainly described. The container 40 accommodates the light source 11, the photodetector 17, and the magnetic field applicator 18. The container 40 further accommodates the first optical fiber 21 and the second optical fiber 23. These optical fibers are components not to be electrified and can be disposed outside the container 40. The first polarizer 12 and the second polarizer 16 are fitted in openings of the airtight container 40, reducing the number of components of the gas sensing apparatus 1.

The gas sensing element 14 is fixed to the container 40 so that the laminate film 142 will be exposed to the atmosphere 30 to be examined. In the configuration example of FIG. 10, the substrate 141 of the gas sensing element 14 is fitted in an opening (not-shown) in the container 40; a part of the substrate 141 is inside the container 40 and the remaining part is exposed to the outside of the container 40. The laminate film 142 on the substrate 141 is exposed to the outside of the container 40.

As a result of protecting the active elements to be electrified within an airtight container as described above, the remaining in the environment to be examined are only components not to be electrified like the gas sensing element 14 and the mirrors 13 and 15. Such an explosion-proof structure is useful particularly for a gas sensing apparatus for sensing a combustible gas.

As set forth above, embodiments of this disclosure have been described; however, this disclosure is not limited to the foregoing embodiments. Those skilled in the art can easily modify, add, or convert each element in the foregoing embodiments within the scope of this disclosure. A part of the configuration of one embodiment can be replaced with a configuration of another embodiment or a configuration of an embodiment can be incorporated into a configuration of another embodiment.

What is claimed is:

1. A gas sensing apparatus, comprising:
a light source;
a photodetector;
a gas sensing element disposed on an optical path from the light source to the photodetector;
a first optical fiber disposed between the light source and the gas sensing element on the optical path;
a second optical fiber different from the first optical fiber and disposed between the gas sensing element and the photodetector on the optical path;
a magnetic field applicator configured to apply a magnetic field to the gas sensing element;
a first polarizer disposed between the first optical fiber and the gas sensing element on the optical path; and
a second polarizer different from the first polarizer and disposed between the gas sensing element and the second optical fiber on the optical path,
wherein the gas sensing element includes, laminated on a substrate, a reflective metal layer, a dielectric optical interference layer, a magnetic metal layer, and a gas sensing layer having optical characteristics that change as a consequence of a reaction of said gas sensing layer to a gas,
wherein the gas sensing element reflects light incoming along the optical path on a sensing face,
wherein each of the first optical fiber and the second optical fiber bends the optical path,
wherein the gas sensing element, the light source, the photodetector, and the magnetic field applicator are disposed on a same side with respect to a virtual plane that is perpendicular to an incident plane of the incoming light to the sensing face of the gas sensing element and includes a point on the optical path where light goes out from the first optical fiber and a point on the optical path where light enters the second optical fiber,
wherein the optical path includes a point to show a directional vector of a light ray including a component parallel to and in a same orientation as a normal vector to the sensing face of the gas sensing element in a section between a point where the light ray goes out from the light source and a point where the light ray goes out from the first optical fiber,
wherein the incoming light to the sensing face of the gas sensing element has a component parallel to and in an opposite orientation to a normal vector to the sensing face of the gas sensing element and a component perpendicular to the normal vector,
wherein the light reflected by the gas sensing element has a component parallel to and in a same orientation as the normal vector and a component perpendicular to the normal vector, and
wherein the optical path includes a point to show a directional vector of a light ray including a component parallel to and in the opposite orientation to the normal vector in a section between a point where the light ray enters the second optical fiber and a point where the light ray enters the photodetector.

2. The gas sensing apparatus according to claim 1,
wherein a directional vector of a light ray emitted from the light source has a component parallel to and in the same orientation as a normal vector to the sensing face of the gas sensing element, and
wherein a directional vector of a light ray entering the photodetector has a component parallel to and in the opposite orientation to the normal vector.

3. The gas sensing apparatus according to claim 1, wherein the light source, the photodetector, the gas sensing element, and the magnetic field applicator are fixed to a same base.

4. The gas sensing apparatus according to claim 1, further comprising:
an airtight container formed to accommodate the light source, the photodetector, and a magnetic field generating element of the magnetic field applicator, wherein the container has a first window disposed between the light source and the gas sensing element on the optical path and a second window disposed between the gas sensing element and the photodetector on the optical path, and wherein a surface of the gas sensing element to receive incoming light is located outside the container.

5. The gas sensing apparatus according to claim 4, wherein the container further accommodates the first optical fiber and the second optical fiber.

6. The gas sensing apparatus according to claim 4, wherein the first window is the first polarizer.

7. The gas sensing apparatus according to claim 4, wherein the second window is the second polarizer.

8. The gas sensing apparatus according to claim 4, wherein the first window is the first polarizer and the second window is the second polarizer.

* * * * *